United States Patent
Heppner et al.

(10) Patent No.: US 10,359,438 B2
(45) Date of Patent: Jul. 23, 2019

(54) WARNING SYSTEM FOR POTENTIALLY ERRONEOUS MEASUREMENT RESULTS IN AN AUTOMATED ANALYZER

(71) Applicant: Siemens Healthcare Diagnostics Products GmbH, Marburg (DE)

(72) Inventors: Daniel Heppner, Frankfurt am Main (DE); David Solbach, Frankfurt (DE); Christian Verhalen, Wiesbaden (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 202 days.

(21) Appl. No.: 15/460,217

(22) Filed: Mar. 15, 2017

(65) Prior Publication Data
US 2017/0269111 A1 Sep. 21, 2017

(30) Foreign Application Priority Data
Mar. 17, 2016 (EP) .................................. 16160973

(51) Int. Cl.
*G01N 35/00* (2006.01)
*G01N 35/04* (2006.01)

(52) U.S. Cl.
CPC . *G01N 35/00623* (2013.01); *G01N 35/00732* (2013.01); *G01N 35/04* (2013.01); *G01N 2035/00277* (2013.01); *G01N 2035/00633* (2013.01); *G01N 2035/00643* (2013.01); *G01N 2035/00841* (2013.01); *G01N 2035/00891* (2013.01); *G01N 2035/0491* (2013.01)

(58) Field of Classification Search
CPC ....... G01N 35/00623; G01N 35/00732; G01N 35/04; G01N 2035/00277; G01N 2035/00633; G01N 2035/00643; G01N 2035/00841; G01N 2035/00891; G01N 2035/0491
See application file for complete search history.

(56) References Cited

U.S. PATENT DOCUMENTS

| | | | | |
|---|---|---|---|---|
| 5,366,896 A | * | 11/1994 | Margrey | G01N 35/00871 436/48 |
| 2011/0086432 A1 | | 4/2011 | Herz et al. | |
| 2012/0064638 A1 | * | 3/2012 | Onomichi | G01N 35/0092 436/501 |
| 2013/0136569 A1 | * | 5/2013 | Rosmarin | G01N 35/0099 414/618 |
| 2014/0141518 A1 | | 5/2014 | Pufahl | |
| 2015/0276781 A1 | | 10/2015 | Riether et al. | |

FOREIGN PATENT DOCUMENTS

| | | |
|---|---|---|
| CN | 102435761 A | 5/2012 |
| EP | 2308588 A2 | 4/2011 |
| EP | 2730927 A1 | 5/2014 |
| EP | 2995959 A1 | 3/2016 |
| JP | 2009300402 A | 12/2009 |

OTHER PUBLICATIONS

European Office Action and Search Report of European Application No. 16160973.0-1553 dated Sep. 19, 2016.

\* cited by examiner

*Primary Examiner* — Benjamin R Whatley
(74) *Attorney, Agent, or Firm* — Dugan & Dugan, PC

(57) ABSTRACT

The present invention lies in the field of automated analyzers and relates to an automated warning system for potentially erroneous measurement results, which may be caused by the loss of a liquid container during a transport process.

11 Claims, 1 Drawing Sheet

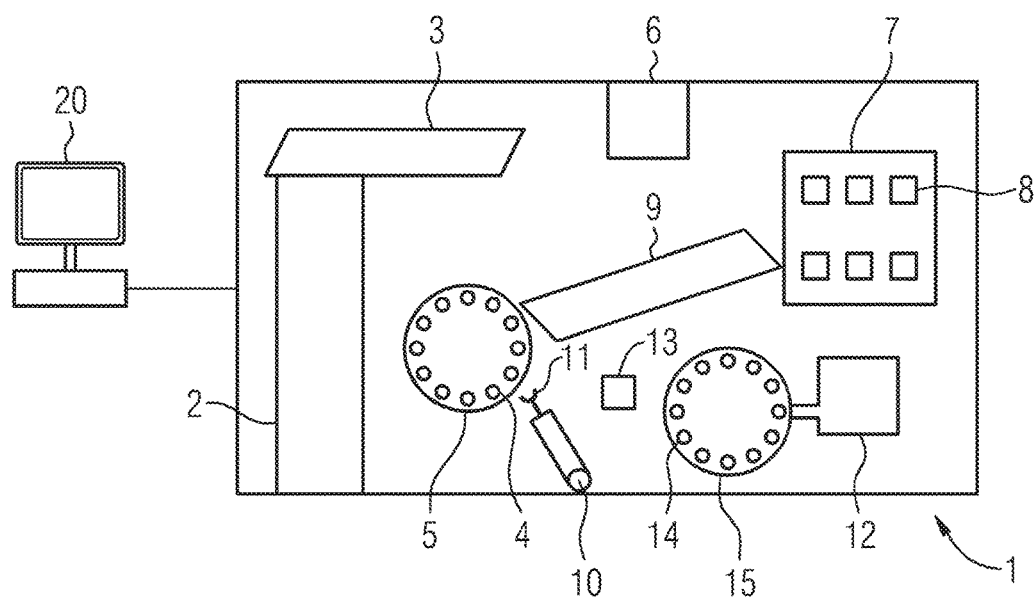

WARNING SYSTEM FOR POTENTIALLY ERRONEOUS MEASUREMENT RESULTS IN AN AUTOMATED ANALYZER

CROSS REFERENCE TO RELATED APPLICATION

This claims priority to European Patent Application No. EP 16160973.0, filed Mar. 17, 2016, which is hereby incorporated by reference herein in its entirety for all purposes.

FIELD

The present invention lies in the field of automated analyzers and relates to an automated warning system for potentially erroneous measurement results, which may be caused by the loss of a liquid container during a transport process.

BACKGROUND

Current analyzers, as are used as a matter of routine in analytics, forensics, microbiology and clinical diagnostics, are able to carry out a multiplicity of detection reactions and analyses with a multiplicity of samples. In order to be able to carry out a multiplicity of examinations in an automated manner, various automatically operating apparatuses for the spatial transfer of measuring cells, reaction containers and reagent liquid containers are required, such as, e.g., transfer arms with a gripper function, transport belts or rotatable transport wheels, and apparatuses for transferring liquids, such as, e.g., pipetting apparatuses. The machines comprise a central control unit which, by means of appropriate software, is able to largely independently plan and work through the work steps for the desired analyses.

Many of the analysis methods used in such analyzers operating in an automated manner are based on optical methods. Measurement systems based on photometric (e.g. turbidimetric, nephelometric, fluorometric or luminometric) or radiometric measurement principles are particularly widespread. These methods enable the qualitative and quantitative detection of analytes in liquid samples without having to provide additional separation steps. The determination of clinically relevant parameters, such as, e.g., the concentration or the activity of an analyte, is often implemented by virtue of an aliquot of a bodily fluid of a patient being mixed simultaneously or in succession with one or more reagent liquids in a reaction vessel, as a result of which a biochemical reaction is put into motion, which brings about a measurable change in an optical property of the test preparation.

The measurement result is, in turn, forwarded into a memory unit by the measurement system and evaluated. Subsequently, the analyzer supplies a user with sample-specific measurement values by way of an output medium, such as, e.g., a monitor, a printer or a network connection.

For the spatial transfer of liquid containers, provision is often made of grippers for capturing, holding and releasing a liquid container, said grippers being attached to a horizontally and vertically movable transfer arm. EP-A2-2308588 describes an exemplary apparatus for transferring tube-shaped reaction vessels (cuvettes) within an automated analyzer. The apparatus comprises a passive, elastically deformable gripper for the force-fit capture and hold of a liquid container and it is suitable to receive an individual cuvette placed in a receiving position, transport said cuvette to a target position and put it down there in a further receiving position. EP-A2-2730927 describes another exemplary apparatus for transferring reagent liquid containers within an automated analyzer.

A problem is that, when transporting liquid containers, there may—during pickup, during the transport itself or else when placing down the container—be an error and the container may be lost. By way of example, a container may fall over or fall out of a transport apparatus and thus come to rest in an uncontrolled manner somewhere in the interior of the analyzer. In so doing, there may be significant contamination in the interior of the analyzer as a result of liquid spraying or flowing out of the container, particularly if this relates to unsealed liquid containers such as, e.g., reaction vessels. A particular problem is that spraying liquid may also enter other liquid containers, such as, e.g., other reaction vessels or reagent liquid containers, as result of which the liquids contained therein or to be dispensed therein are contaminated. Since the measurement of a contaminated sample or the use of a contaminated reagent may lead to erroneous measurement results, it is necessary to ensure that, firstly, the loss of a liquid container is automatically identified by the analyzer and that, secondly, a user is informed about the incident.

It is known that various sensor systems are used for identifying a loss of a liquid container, for example, Hall sensor systems at the gripper apparatuses, photoelectric barrier systems in the receiving positions for the liquid containers, or else cameras.

A known automated analyzer is configured in such a way that, if a loss of a reaction vessel is identified, it is only the measurements for reaction mixes in those reaction vessels which are already in the measurement station that are still completed, while all other planned measurements are stopped. Only once a user has ensured that there has been no contamination or that said contamination has been removed can the analyzer continue anew with working through the planned measurements.

This configuration is disadvantageous in that a timely user intervention is required for each incident in which a reaction vessel is lost, i.e., even in those incidents in which no contamination arose because, for example, an empty reaction vessel was lost, in order to lift the break in operation of the analyzer as quickly as possible. This system configuration offers a high degree of safety but requires regular attendance of a user and hence a high maintenance outlay, or causes a reduction in the overall throughput of the analyzer if a user cannot process the incident in a timely manner.

SUMMARY

Therefore, the present invention is based on the object of providing an automated analyzer with a relatively low maintenance outlay but unchangingly high degree of safety. According to the invention, this object is achieved by virtue of the analyzer being operated by a method in which a transport process of a liquid container is monitored and in which—provided the loss of a liquid container during the transport process is determined—a check is initially carried out as to whether the lost liquid container was filled with liquid. Only if it is determined that the liquid container was filled with liquid are all other liquid containers situated in a receiving position of the automated analyzer labeled as potentially contaminated and each measurement result of a measurement of a property of a liquid sample which contains at least one liquid from a liquid container labeled as potentially contaminated or which is contained in a liquid container labeled as potentially contaminated is labeled as potentially erroneous.

This is advantageous in that a user is only in fact warned if there is in fact the danger of contamination by spraying or escaping liquid. Moreover, this procedure is advantageous in that the measurements which are running or planned at the time of the incident may be continued without interruption, increasing the overall throughput of the analyzer. Labeling the potentially erroneous measurement results allows a user at any time after the completion of the measurements to check whether the measurement results are plausible or whether, possibly, an error may be present. The targeted assessment of the labeled measurement results by a user ensures a high level of safety and, in the ideal case, leads to the measurement results being available at the earliest possible time despite an incident. The user will only have to initiate the repeated measurement of a sample in the case of doubt.

Thus, the subject matter of the invention is a method for operating an automated analyzer comprising
  an apparatus for measuring a property of a liquid sample,
  a multiplicity of receiving positions for liquid containers,
  at least one apparatus for transporting a liquid container from a first receiving position into a second receiving position, and
  a data memory, in which a data record with information is stored for each liquid container situated in the analyzer, said data record facilitating a unique identification of a liquid container.
The method comprises the following steps:
  monitoring a transport process of a liquid container from a first receiving position into a second receiving position with the aid of one or more sensors; and
  provided the loss of a liquid container during the transport process is determined—checking whether the lost liquid container was filled with liquid; and wherein
  provided it is determined that the lost liquid container was filled with liquid—all other liquid containers situated in a receiving position of the automated analyzer are labeled by virtue of further information labeling the liquid container as potentially contaminated being added to the data record of each liquid container situated in a receiving position of the analyzer; and wherein
  each measurement result of a measurement of a property of a liquid sample which contains at least one liquid from a liquid container labeled as potentially contaminated or which is contained in a liquid container labeled as potentially contaminated is labeled as potentially erroneous.

Monitoring a transport process of a liquid container from a first receiving position into a second receiving position with the aid of one or more sensors may be carried out with the aid of any suitable sensor system. By way of example, suitable sensor systems are mechanical, resistive, piezoelectric, optical, capacitive, inductive or magnetic sensor systems, such as, e.g., Hall sensor systems at the gripper apparatuses, photoelectric barrier systems in the receiving positions for the liquid containers or else cameras which track the spatial transfer. The ascertained measurement variables are compared to values corresponding to a correct transport process which are ascertained in advance. Deviations from the intended values indicate the loss of a liquid container during the transport process.

Provided the loss of a liquid container during the transport process is determined, a check is initially carried out as to whether the lost liquid container was filled with liquid. This is preferably carried out by reading a data memory, in which a data record with information facilitating a unique identification of a liquid container is stored for each liquid container situated in the analyzer. This data memory is continuously updated and, in addition to an identification number for a specific liquid container, contains, e.g., container-specific information (e.g., type of container, e.g., reaction vessel or reagent liquid container; content of the container, e.g., type of reagent, sample identification number) and status-specific information (e.g., fill level or fill amount, spatial localization), wherein said status-specific information is continuously updated.

Provided it is determined during this checking that the lost liquid container was filled with liquid, all other liquid containers situated in a receiving position of the automated analyzer are labeled by virtue of further information labeling the liquid container as potentially contaminated being added to the data record, stored in the data memory, of each liquid container situated in a receiving position of the analyzer. Liquid containers situated in a receiving position of the automated analyzer are those which are already provided for specific use in the analyzer and already identified and captured in the data memory. This explicitly does not mean those liquid containers which are stored for future use in an unordered and non-identified manner in a storage container, for example, in the form of bulk goods.

Subsequently, each measurement result of a measurement of a property of a liquid sample which contains at least one liquid from a liquid container labeled as potentially contaminated or which is contained in a liquid container labeled as potentially contaminated is labeled as potentially erroneous. Expressed differently: all measurement results which were obtained using a liquid container labeled as potentially contaminated (e.g., a reaction vessel that was empty at the time of the incident) or a liquid (e.g., reagent, primary sample or reaction mix) from a liquid container labeled as potentially contaminated inherit the warning label.

Labeling a measurement result as "potentially erroneous" does not mean that the measurement result is necessarily erroneous but merely supplies a user with information that this measurement result requires further checking.

If the check as to whether the lost liquid container was filled with liquid determines that the lost liquid container was empty, no further information which would label the liquid container as potentially contaminated is added to the data record, stored in the data memory, of each liquid container situated in a receiving position of the analyzer.

Preferably, all measurements of properties of liquid samples in progress at the time at which it is determined that a lost liquid container was filled with liquid, are continued without interruption until a measurement result is available. In other words: all planned measurements are completed despite the incident.

Further subject matter of the present invention relates to an automated analyzer comprising
  an apparatus for measuring a property of a liquid sample,
  a multiplicity of receiving positions for liquid containers,
  at least one apparatus for transporting a liquid container from a first receiving position into a second receiving position,
  a data memory, in which a data record with information is stored for each liquid container situated in the analyzer, said data record facilitating a unique identification of a liquid container, and further a control device configured such that it controls the above-described method according to the invention for operating the automated analyzer.

In particular, the control device of the automated analyzer according to the invention is configured such that it controls a method comprising the following steps:
monitoring a transport process of a liquid container from a first receiving position into a second receiving position with the aid of one or more sensors; and
provided the loss of a liquid container during the transport process is determined—checking whether the lost liquid container was filled with liquid; and wherein
provided it is determined that the lost liquid container was filled with liquid—all other liquid containers situated in a receiving position of the automated analyzer are labeled by virtue of further information labeling the liquid container as potentially contaminated being added to the data record of each liquid container situated in a receiving position of the analyzer; and wherein
each measurement result of a measurement of a property of a liquid sample which contains at least one liquid from a liquid container labeled as potentially contaminated or which is contained in a liquid container labeled as potentially contaminated is labeled as potentially erroneous.

The apparatus for measuring a property of a liquid sample is preferably an apparatus for measuring an optical property, such as, e.g., a photometer, such as, e.g., a spectrophotometer, a nephelometer or a turbidimeter, or a fluorometer or a luminometer. However, the measurements of other physical properties of a sample are likewise possible, such as, e.g., the measurement of radioactive radiation (radiometer).

A "receiving position for a liquid container" means a location provided for the placement of a liquid container. Here, this is often a receiving apparatus, adapted in terms of structure, which facilitates stable storage of the liquid container, such as, e.g., sleeves, into which a specifically designed liquid container may be inserted in an interlocking manner. In an automated analyzer, provision is predominantly made for receiving positions for primary sample vessels, for reaction vessels (usually in the form of transparent, tube-shaped cuvettes) and for reagent liquid containers. The receiving positions are situated at defined positions, such as, e.g., in movable receiving devices, such as, e.g., rotatable cuvette or reagent plates, or stationary storage containers.

A primary sample vessel, such as, e.g., a blood sampling tube, contains the sample liquid to be analyzed. Liquids to be analyzed are, e.g., bodily fluids such as blood, plasma, serum, urine, amniotic fluid, etc., wastewater samples or cell culture supernatants. A reagent liquid container contains at least one liquid containing one or more substances for detecting one or more analytes, such as, e.g., antibody solutions, dye solutions, etc. Furthermore, a reagent liquid container may have a multi-chamber configuration and contain a plurality of different reagent liquids. A reaction vessel, such as, e.g., a transparent, tube-shaped cuvette, is provided for the provision of a reaction mix, i.e., a mixture of primary sample and reagent liquid(s).

An apparatus for transporting a liquid container from a first receiving position into a second receiving position is preferably a gripper fastened to a transfer arm which is horizontally and vertically displaceable or swivellable.

The gripper may be part of a mechanical, magnetic, pneumatic or adhesive gripper system. A mechanical gripper may be configured as a one-finger gripper, two-finger gripper or multi-finger gripper and may have a rigid, articulated or elastic embodiment. Preferably, the gripper is a passive clamping gripper for force-fit capturing and holding of a liquid container. The latter may have an integral and elastically deformable configuration. The gripper preferably is in a tensioned state such that there is a snap-effect when said gripper is pressed against a liquid container with sufficient force and the gripper opens, and grips around and holds the liquid container. Conversely, the gripper only opens again, and releases the liquid container, when the gripper is moved away from a fixed liquid container with sufficient force.

A data record with information facilitating a unique identification of a liquid container is stored in the data memory for each liquid container situated in the analyzer. This data memory is continuously updated and, in addition to an identification number, contains, e.g., container-specific information (e.g., type of container, e.g., reaction vessel or reagent liquid container; content of the container, e.g., type of reagent, sample identification number) and status-specific information (e.g., fill level or fill amount, spatial localization) for a specific liquid container, wherein said status-specific information is updated continuously. In particular, the information which labels the liquid container as potentially contaminated when a loss of a liquid container filled with liquid was determined is also added to a data record, contained in the data memory, for a specific liquid container.

The sensor or sensors for monitoring a transport process of a liquid container from a first receiving position into a second receiving position may be mechanical, resistive, piezoelectric, optical, capacitive, inductive or magnetic sensors.

Hall sensor systems on the gripper of the transport apparatus, photoelectric barrier systems in the receiving positions for the liquid containers or else cameras which track the spatial transfer are preferred.

An analyzer according to the invention preferably further comprises a screen for displaying measurement results.

In this case, the control device may be configured in such a way that it controls that a measurement result labeled as potentially erroneous is depicted in a different color than a measurement result which is not labeled as potentially erroneous. By way of example, measurement results labeled as potentially erroneous may be displayed in a red color while non-labeled measurement results are depicted in a black color.

Alternatively, or additionally, the control device may be configured in such a way in this case that it controls that a measurement result labeled as potentially erroneous is depicted together with a warning symbol, for example, a pictogram. By way of example, measurement results labeled as potentially erroneous may be depicted together with an exclamation mark, while non-labeled measurement results are depicted without an exclamation mark.

An analyzer according to the invention may further comprise an additional output medium, wherein the control device is then further configured in such a way that it controls that the output medium generates a visually and/or acoustically perceivable signal if the loss of a filled liquid container during the transport process is determined.

The output medium may be a loudspeaker, wherein the controller is then configured in such a way that a determined loss of a filled liquid container during a transport process is indicated in the form of an acoustic warning signal. The output medium may also be a warning lamp which is attached to the analyzer in a manner visible from the outside, with the controller then being configured in such a way that a determined loss of a filled liquid container during a transport process is indicated in the form of a light signal.

This ensures that a user is informed about an incident and may adopt necessary measures for remedying possible contamination in a timely manner.

BRIEF DESCRIPTION OF THE DRAWINGS

Below, the invention is explained on the basis of a drawing.

In detail:

FIG. 1 shows an automated analyzer according to the invention.

DETAILED DESCRIPTION

FIG. 1 is a schematic illustration of an automated analyzer 1 with some components contained therein. Here, only the most important components are illustrated in a much simplified manner in order to explain the basic functionality of the automated analyzer 1 without depicting the individual parts of each component in detail.

The automated analyzer 1 is embodied to carry out very different types of analyses of blood or other bodily fluids in a fully automated manner, without this requiring activities by a user. Necessary interventions of a user instead are restricted to servicing or repairing and refill work, for example, if cuvettes need to be refilled or liquid containers need to be replaced.

The patient samples are fed to the automated analyzer 1 in primary sample vessels via a feed track 2 on carriages not depicted in any more detail. Information concerning the analyses to be carried out for each sample may, for example, be transferred by means of barcodes which are attached to the sample vessels and which are read in the automated analyzer 1. With the aid of a first pipetting apparatus 3, sample aliquots are removed from the sample vessels by means of a pipetting needle.

The sample aliquots are likewise fed to cuvettes (not depicted in any more detail), which are arranged in receiving positions 4 of a rotatable incubation device 5 which is temperature controlled to 37° C. The cuvettes are removed from a cuvette storage container 6, in which the cuvettes are present in an unordered state as bulk goods. A data record for an individual cuvette is only generated when said cuvette is removed and said cuvette is placed into a receiving position 4, said data record initially containing information that this relates to a cuvette and the receiving position in which it has been placed. Reagent vessels 8 with various reagent liquids are stored in the reagent vessel storage container 7, which is cooled to approximately 8-10° C. Reagent liquid is taken from a reagent vessel 8 by means of the pipetting needle of a second pipetting apparatus 9 and administered into a cuvette, which already contains a sample aliquot, for providing a reaction mix. By means of the transfer arm 10, the cuvette with the reaction mix is taken from a receiving position 4 of the incubation device 5 with a gripper 11 and transferred to a shaking device 13 for mixing the reaction mix. After completing the mixing process, the cuvette is transported onward into a receiving position 14 of the rotatable receiving apparatus 15 for the photometric measurement station 12, where the absorption of the reaction mix is measured. By way of example, a filled cuvette may be lost during this transport process or else during the shaking. The loss is detected by a Hall sensor (not depicted in any more detail), which is attached between the transfer arm 10 and a gripper 11, and/or by a photoelectric barrier (likewise not depicted in any more detail) at the receiving position 14 of the receiving apparatus 15.

The entire process is controlled by a control unit 20, such as, e.g., a computer connected by way of a data line, supported by a multiplicity of further electronic circuits and microprocessors, not depicted in any more detail, within the automated analyzer 1 and the components thereof.

LIST OF REFERENCE SIGNS

1 Analyzer
2 Feed track
3 Pipetting apparatus
4 Receiving position
5 Incubation device
6 Cuvette storage container
7 Reagent vessel storage container
8 Reagent vessel
9 Pipetting apparatus
10 Transfer arm
11 Gripper
12 Measurement station
13 Shaking device
14 Receiving position
15 Receiving apparatus
20 Control unit

What is claimed is:

1. An automated analyzer comprising:
photometric or radiometric apparatus for measuring a property of a liquid sample,
a multiplicity of first and second receiving positions for liquid containers, the photometric or radiometric apparatus positioned to measure the property of a liquid sample contained in a liquid container located in one of the second receiving positions,
at least one apparatus for transporting a liquid container from a first receiving position into a second receiving position of the multiplicity of first and second receiving positions, the at least one apparatus for transporting the liquid container comprising a transfer arm,
a data memory, in which a data record with information is stored for each liquid container situated in the analyzer, the data record facilitating a unique identification of each liquid container, and
a control device configured such that it controls a method comprising the following steps:
monitoring a transport process of the liquid container from the first receiving position into the second receiving position with the aid of one or more sensors to determine whether the liquid container has been lost during the transport process;
in response to determining a loss of the liquid container during the transport process, checking a data record in the data memory corresponding to the lost liquid container to determine whether the lost liquid container was filled with liquid;
in response to the checking having determined that the lost liquid container had been filled with liquid:
labeling all other liquid containers situated in a respective first or second receiving position of the automated analyzer as potentially contaminated by updating the data record of each of the other liquid containers; and
labeling as potentially erroneous each measurement result of a measurement of the property of a liquid sample which contains at least one liquid from a liquid container labeled as potentially contaminated or which is contained in a liquid container labeled as potentially contaminated; and continuing without interruption until a measurement result is available for all measurements of properties of liquid samples in progress at the time a lost liquid container is determined to have been filled with liquid.

2. A method for operating the automated analyzer of claim 1, comprising:

monitoring a transport process of a liquid container from a first receiving position into a second receiving position with the aid of one or more sensors to determine whether the liquid container has been lost during the transport process;

in response to determining a loss of the liquid container during the transport process, checking a data record in a data memory corresponding to the lost liquid container to determine whether the lost liquid container was filled with liquid;

in response to the checking having determined that the lost liquid container had been filled with liquid:

labeling all other liquid containers situated in a respective first or second receiving position of the automated analyzer as potentially contaminated by updating the data record of each of the other liquid containers; and labeling as potentially erroneous each measurement result of a measurement of a property of a liquid sample which contains at least one liquid from a liquid container labeled as potentially contaminated or which is contained in a liquid container labeled as potentially contaminated; and continuing without interruption until a measurement result is available for all measurements of properties of liquid samples in progress at the time a lost liquid container is determined to have been filled with liquid.

3. The method as claimed in claim 2, wherein, in response to the checking having determined that the lost liquid container was empty, not labeling all the other liquid containers as potentially contaminated.

4. The method as claimed in claim 2, wherein, in response to the checking having determined that the lost liquid container was filled with liquid, generating a visually or acoustically perceivable signal.

5. The automated analyzer as claimed in claim 1, wherein the apparatus for measuring a property of a liquid sample is a photometer.

6. The automated analyzer as claimed in claim 1, wherein the multiplicity of first and second receiving positions for receiving liquid containers comprise receiving positions for receiving respectively one tube-shaped reaction vessel or receiving positions for receiving respectively one reagent liquid container.

7. The automated analyzer as claimed in claim 1, wherein the apparatus for transporting a liquid container from a first receiving position into a second receiving position further comprises a gripper fastened to the transfer arm which is horizontally and vertically displaceable.

8. The automated analyzer as claimed in claim 1, wherein the one or more sensors for monitoring the transport process of a liquid container from a first receiving position into a second receiving position are selected from the group of mechanical, resistive, piezoelectric, optical, capacitive, inductive or magnetic sensors.

9. The automated analyzer as claimed in claim 1, which further comprises a screen for displaying measurement results and wherein the control device is further configured to depict a measurement result labeled as potentially erroneous in a different color than a measurement result which is not labeled as potentially erroneous.

10. The automated analyzer as claimed in claim 1, which further comprises a screen for displaying measurement results and wherein the control device is further configured to depict a measurement result labeled as potentially erroneous with a warning symbol.

11. The automated analyzer as claimed in claim 1, which further comprises an output medium and wherein the control device is further configured to control the output medium to generate a visually or acoustically perceivable signal if the loss of a filled liquid container during the transport process is determined.

* * * * *